(12) United States Patent  
Grudke et al.

(10) Patent No.: US 12,186,464 B2  
(45) Date of Patent: Jan. 7, 2025

(54) COOLING UNIT FOR A HEAT EXCHANGER

(71) Applicant: ResuSciTec GmbH, Freiburg (DE)

(72) Inventors: Jürgen Grudke, Freiburg (DE); Christoph Benk, Freiburg (DE)

(73) Assignee: RESUSCITEC GMBH, Freiburg (DE)

( * ) Notice: Subject to any disclaimer, the term of this patent is extended or adjusted under 35 U.S.C. 154(b) by 680 days.

(21) Appl. No.: 17/438,368

(22) PCT Filed: Mar. 11, 2020

(86) PCT No.: PCT/EP2020/056455  
§ 371 (c)(1),  
(2) Date: Sep. 10, 2021

(87) PCT Pub. No.: WO2020/182856  
PCT Pub. Date: Sep. 17, 2020

(65) Prior Publication Data  
US 2022/0152283 A1    May 19, 2022

(30) Foreign Application Priority Data  
Mar. 11, 2019 (DE) ............ 10 2019 203 253.2

(51) Int. Cl.  
*A61M 1/16* (2006.01)  
*A61F 7/00* (2006.01)  
(Continued)

(52) U.S. Cl.  
CPC ......... *A61M 1/1698* (2013.01); *A61F 7/0085* (2013.01); *A61M 1/32* (2013.01);  
(Continued)

(58) Field of Classification Search  
CPC .... A61M 1/1698; A61M 3/32; A61M 1/3666; A61M 2205/3606; A61M 2205/364;  
(Continued)

(56) References Cited

U.S. PATENT DOCUMENTS

2013/0013033 A1* 1/2013 Lowe ................ A61F 7/02  
607/104  
2014/0371552 A1  12/2014 Gerlitz et al.

FOREIGN PATENT DOCUMENTS

DE 102017211671 A1 1/2019  
EP 3079737 B1 7/2018  
GB 2448478 A * 10/2008 ............. A47J 36/28

OTHER PUBLICATIONS

Wilke, Cooling Unit for a Heat Exchanger . . . , Jun. 18, 2015, WO2015086147A1, Whole Document (Year: 2015).*

(Continued)

*Primary Examiner* — Larry L Furdge  
(74) *Attorney, Agent, or Firm* — Fitch, Even, Tabin & Flannery LLP

(57) ABSTRACT

The invention is a cooling unit for a heat exchanger integrated in an oxygenator for the purpose of controlling the temperature of blood conveyed in an extracorporeal blood circuit. The cooling unit has a reservoir in which a liquid is stored, a reaction vessel comprises a reactant and which, in conjunction with the liquid, is able to initiate an endothermal reaction. A fluidic access is generated between the reservoir and the reaction vessel. A fluid line extends at least in part inside the reaction vessel which has an inlet line and outlet line connected to be fluid-tight to a hose system of the heat exchanger.

17 Claims, 3 Drawing Sheets

(51) Int. Cl.
*A61M 1/32* (2006.01)
*A61M 1/36* (2006.01)
*A61F 7/12* (2006.01)

(52) U.S. Cl.
CPC ... *A61M 1/3666* (2013.01); *A61F 2007/0056* (2013.01); *A61F 2007/0093* (2013.01); *A61F 7/12* (2013.01); *A61M 2205/3606* (2013.01); *A61M 2205/364* (2013.01); *A61M 2205/366* (2013.01)

(58) Field of Classification Search
CPC ... A61M 2205/366; A61F 7/0085; A61F 7/12; A61F 2007/0056; A61F 2007/0093
See application file for complete search history.

(56) References Cited

OTHER PUBLICATIONS

International Search Report for PCT/EP2020/056455, mailed Jun. 17, 2020; English translation submitted herewith (5 pgs.).

\* cited by examiner

COOLING UNIT FOR A HEAT EXCHANGER

CROSS-REFERENCE TO RELATED APPLICATIONS

Reference is made to International Application No. PCT/EP2020/056455, filed Mar. 1, 2020, which claims priority to German Patent Application No. 10 2019 203 253.2, filed Mar. 11, 2019, the contents of which are incorporated herein by reference in their entirety.

BACKGROUND OF THE INVENTION

Field of the Invention

The invention relates to a cooling unit for a heat exchanger, preferably for a heat exchanger integrated in an oxygenator for the purpose of controlling the temperature of blood conveyed in an extracorporeal blood circuit, with a reservoir in which a liquid is stored, a reaction vessel which comprises a reactant and which, in conjunction with the liquid, is able to initiate an endothermal reaction, means for generating a fluidic access between the reservoir and the reaction vessel, and a fluid line which extends at least in part inside the reaction vessel, and which has an inlet line and outlet line, which are each connectable or connected in a fluid-tight manner to a hose system of the heat exchanger, and which, together with the hose system of the heat exchanger, forms at least part of a fluid circuit.

Description of the Prior Art

It is known to use the heat or cold released in exothermal or endothermal chemical reactions by technical means, by thermal coupling. In the case of endothermal reactions, in which cold is released, there are a plurality of applications which are briefly outlined below.

In the context of cardiac surgery or intensive medicine, in particular for treating at least one of acute cardiac and lung failure, heart-lung machines are used by which the pumping function of the heart and the lung function are able to be replaced for a limited time period. In this case, the blood leaves the body via an extracorporeal blood circuit in the form of a hose system, is enriched with oxygen by an oxygenator which is part of the heart-lung machine and is returned back into the body. At the same time the oxygenator undertakes the function of the lungs and supplies the blood, not only with vital oxygen, but at the same time removes the carbon dioxide ($CO_2$) produced by metabolic processes.

The majority of oxygenators used nowadays additionally have a heat exchanger, the blood flowing through is able to be heated but, in particular, cooled thereby. Thus interventions on the heart generally take place under hypothermic conditions, which are the blood is cooled to a greater or lesser extent since the lowering of the body temperature reduces the metabolic activity of the cells and increases the ischemia tolerance of the affected tissues and organs.

So-called hypothermia devices serve as cold sources in which generally cooled water is generated as the cooling liquid, and used in order to cool via a heat exchanger the blood flowing through the oxygenator, to remove the thermal energy thereof in a controlled manner. Commercially available hypothermia devices are large and heavy-weight operating units, generally mounted on rollers with heating and cooling systems thereof being supplied via electrical infrastructure and thus not suitable to be used in the field.

Modern hypothermia devices, due to a compact design and a substantially autonomous supply of power and cooling water, permit a portable use, independently of a supply of electrical power and water. Such hypothermia devices provide fluid-tight connections for a heat exchanger integrated in the oxygenator, so that they may be used in a modular or integrated manner in combination with an oxygenator.

The principle of refrigeration in such substantially autonomously operating modern hypothermia devices is based on an endothermal chemical reaction generally between ammonium nitrate, calcium-ammonium nitrate or urea and water. Frequently urea is used as a chemical component in cold packs in order to generate a rapid cooling effect. These cold packs generally have two separate regions, with urea being located in one of them and water being located in the other thereof. If the separation is broken, the urea is dissolved in the water. Since the lattice energy of urea is greater than the hydration energy, the dissolving process removes energy from the surroundings and cools it down. See Robert T. Sataloff: *Sataloffs Comprehensive Textbook of Otolaryngology*. Jaypee Brothers, 2016, ISBN 978-93-5152745-9, p 412.

US published patent application 2014/0371552 A1 discloses a blood sugar measuring device which is able to be positioned, non-invasively onto the skin surface of a patient, which comprises a cooling device, a temperature measuring device and an infrared radiation detector. For the purpose of measuring blood sugar, the skin surface is reduced to a predetermined temperature by the cooling device and infrared radiation, emitted or absorbed by the skin surface, is measured. The cooling device has two chambers which are sealed in a fluid-tight manner and which are directly adjacent to one another with one chamber being filled with urea and the other chamber being filled with water. A partition separating both chambers in a fluid-tight manner may be locally perforated a spring-loaded pin, so that the water pours into the chamber of the urea, initiating an endothermal reaction which draws thermal energy from the surroundings and cools the skin surface to be measured in a predeterminable manner.

A device for controlling temperature based on a chemical reaction and the use thereof as a temperature control unit for a heat exchanger is disclosed in the publication DE 10 2017 211 671 A1. The disclosed device uses a container which is partially filled with granular urea and a second container, which has a deformable container wall, is filled with water incorporated therein. For the purposes of cooling, the water pours out of the second container into the first container and reacts with the urea, forming a positive reaction enthalpy which may be used by technical means providing thermal coupling.

SUMMARY OF THE INVENTION

The invention is configured as a cooling unit for use as a heat exchanger. Preferably the heat exchanger is integrated in an oxygenator for the purpose of controlling the temperature of blood conveyed in an extracorporeal blood circuit, having a reservoir in which liquid is stored, a reaction vessel which comprises a reactant and which, in conjunction with the liquid, is able to initiate an endothermal reaction, a functional device which provides a fluidic access between the reservoir and the reaction vessel, and a fluid line which extends at least in part inside the reaction vessel having an inlet line and outlet line, which are each connectable or connected in a fluid-tight manner to a hose system of the heat exchanger, and which, together with the hose system of the heat exchanger, forms at least part of a fluid circuit, which is as compact as possible, lightweight and which operates autonomously, in order to permit manual portability. The cooling unit is implemented by means which are as simple and cost-effective as possible which provides the possibility of forming subcomponents which are configured at least in a modular manner, as at least one of a disposable product and as a disposable item. The quantity of at least one of heat and cold which is able to be discharged from the device is designed provides, in the shortest possible time, generation of at least one of a cooling and heating capacity which is as great as possible.

The cooling unit according to the invention has an expansion tank with an overflow, into which the liquid from the reservoir flows after fluidic access has been generated between reservoir and reaction vessel. The fluidic access is produced to be able to provide at least one of perforating and opening locally the reservoir. The overflow constitutes a fluid connection to the reaction vessel through which a proportion, preferably the main proportion, of the stored liquid passes into the reaction vessel in order to initiate the endothermal reaction with the reactant, preferably in the form of granular urea. The fluid line is fluidically connected to the expansion tank, into which the remaining proportion of the stored liquid from the reservoir passes. The remaining proportion of the stored liquid is that liquid portion which, due to the geometry of the overflow relative to the holding capacity of the expansion tank, does not flow into the reaction vessel. At least one of a non-return valve and return flow valve is preferably arranged along the fluid connection of the overflow, to prevent the liquid, which has passed through the overflow into the reaction vessel, from flowing back into the expansion tank. Additionally a fluid pump is located outside the reaction vessel along the fluid line which runs at least partially inside the reaction vessel, so that liquid from the expansion tank is suctioned into the fluid line extending at least in part inside the reaction vessel.

The fluid line extending at least in part inside the reaction vessel also extends in a fluid-tight manner through the reaction vessel wall delimiting the reaction vessel outwardly and forms a fluid line portion which is denoted hereinafter as the outlet line and which is configured in the form of a flexible hose line. The fluid line extending in the interior is produced at least in sections from metal, preferably from aluminium, for the purpose of the best possible heat transfer to the surrounding medium inside the reaction vessel. In order to ensure a heat transfer contact surface which is as large as possible between the fluid line and the liquid present in the interior of the reaction vessel, the line path of the fluid line in the interior of the reaction vessel is selected to be as long as possible. To this end, the fluid line extending in the interior of the reaction vessel which is preferably configured, at least in sections, helically or in a helical manner.

A fluid pump is arranged along the outlet line leading outwardly from the reaction vessel and is preferably a peristaltic pump, with a circulation of the flow of fluid being established in the fluid line by the exertion of peristaltic pressure acting from the outside on the hose line such that the liquid, which is located inside the expansion tank, is suctioned through the fluid line. Alternatively, the fluid pump is arranged upstream of the aforementioned fluid line portion which is configured helically or in a helical manner along a fluid line portion leading outside the reaction vessel.

Optionally a filter unit, preferably in the form of a bacterial filter, is attached along the outlet line leading out of the reaction vessel so that contamination of the heat exchanger in the oxygenator by germs, for example *Legionella*, is avoided thereby.

The outlet line of the fluid line is also preferably connected via a releasable fluid-tight coupling to the inlet of a hose system, which is thermally coupled to a heat exchanger integrated inside an oxygenator.

The fluidic outlet of the hose system, which is thermally coupled to the heat exchanger, is preferably connected via a releasable fluid-tight coupling to the inlet line of the fluid line which feeds into the expansion tank. Thus the expansion tank, the fluid line and also the hose system of the heat exchanger form a self-contained fluid circuit, along which the liquid, which serves as the heat transfer liquid of the heat exchanger, circulates. Specifically this liquid portion, which serves as the heat transfer liquid, comes from the liquid stored inside the reservoir, to pour into the expansion tank after at least one of the corresponding local perforation and opening of the reservoir by use of the functional means, to be described hereinafter in more detail.

Due to a limited receiving volume inside the expansion tank, which is smaller than the holding capacity of the reservoir, the greatest liquid portion flows via the overflow along the fluid connection into the reaction vessel in which the reactant, preferably in the form of granular urea, is stored. Alternative reactants are also suitable, which together with a liquid, preferably water draw thermal energy from the surroundings to form an endothermal chemical reaction.

The quantity of liquid stored inside the reservoir is measured such that the liquid portion flowing out via the overflow and the fluid connection into the reaction vessel is at least 70%. The remaining proportion of the liquid is retained inside the expansion tank which, as described above, serves as the heat transfer liquid for the heat exchanger connected fluidically to the cooling unit which is configured according to the invention. The distribution of the quantity of liquid, which is at least one of discharged from and discharged out of the expansion tank via the fluid connection into the reaction vessel. The distribution of the quantity is able to be predetermined, in particular, by the height of the pipeline at which the fluid connection protrudes into the expansion tank.

In order not to impede the filling of at least the reaction vessel and the discharge process of the liquid from the expansion tank into the reaction vessel through the fluid connection, due to a pressure increase which would otherwise form inside the reaction vessel, the reaction vessel provides at least one vented opening into the surroundings, in the upper region in the vicinity of the expansion tank. The vented opening preferably has a hydrophobic filter insert through which an uncontrolled escape of liquid, caused by tilting or moving the cooling unit, may be prevented.

An agitator is also arranged inside the reaction vessel for assisting and homogenizing the chemical, endothermal reaction between the liquid and the granular reactant. The agitator is able to be driven via a mechanical interface, for example by a gear drive with a drive motor, arranged outside the reaction vessel. In order to ensure that no liquid portions are able to pass back from the reaction vessel into the expansion tank, in particular since this would contaminate the liquid located inside the expansion tank, a non-return valve is arranged along the fluid connection.

For the purpose of a handling of the cooling unit configured according to the invention which is as simple and as error-free as possible, the reservoir is preferably a liquid-containing bag. For reasons of mechanical protection, the liquid-containing bag is also located inside a first housing which is arranged vertically above a second housing surrounding at least the expansion tank. A third housing, encompassing the reaction vessel, is arranged vertically below the second housing surrounding the expansion tank. Optionally the second and third housings are configured integrally. A spacer is additionally arranged between the first and the second housing, which ensures a predetermined vertical spacing between the reservoir contained in the first housing and the functional means which is preferably fixedly attached to or inside the expansion tank.

The functional means is a sharp-edged object and is preferably arranged vertically below the reservoir.

The spacer, which vertically spaces apart the reservoir in the vertical direction relative to the expansion tank and which prevents a direct contact between the reservoir and the sharp-edged functional means, is mounted between the first and second housing, preferably such that the spacer is able to be separated from the stack assembly to the side, for example by being manually pulled out. After removing the spacer, the reservoir drops vertically down, due to its weight and as a result of gravitational force, comes into contact with the sharp-edged functional means, whereby the reservoir is at least one of mechanically perforated and opened locally, so that the liquid stored in the reservoir pours entirely into the expansion tank. At the same time as a result of at least one vertical lowering and dropping of the reservoir, and the filling of the expansion tank and reaction vessel associated therewith, the fluid pump and also the drive motor operate for activating the agitator inside the reaction vessel.

The first housing, surrounding the reservoir, and the second housing, arranged vertically therebelow, are configured relative to their sides, which vertically and directly face one another, so that, after removing the spacer, both housings slide into one another in a mechanically defined manner, for example in the manner of a peripheral tongue-groove connection which forms a fixed mechanical joint.

The cooling unit according to the invention provides a rapid and efficient large cooling capacity within a very short time, which requires no further necessary supply of electrical power apart from powering the fluid pump and the drive motor. Due to the limited energy requirement, the necessary electrical energy may be made available by a battery.

A preferred embodiment of the cooling unit, according to the invention, provides a modular construction so that the electrical components, such as the fluid pump and drive motor in addition to the required control unit and electrical energy source, are located in a single housing which is a modular configuration. The first housing containing the reservoir, the spacer, the second housing comprising the expansion tank, and the third housing comprising the reaction vessel are each modular units which are stackable vertically on top of one another and may be disposed of after use as disposable articles. Preferably, it is advantageous to produce at least the reservoir and the reaction vessel from a plastics lightweight packaging material, for example tightly compressed polystyrene, which may be sent for material recycling. In order to ensure that the reaction vessel is fluid-tight, the inner wall of the reaction vessel, coming into contact with the liquid, is provided with a liquid-tight coating. Additionally, the coating material may be selected such that it is chemically inert relative to the liquid-reactant mixture and the chemical products being formed therefrom.

For reasons of sustainability and careful disposal, it is additionally advantageous to provide a binding agent inside the reaction vessel, which triggers a gel-forming process when reacting with at least one of the liquid and the liquid-reactant mixture which is formed, After using the cooling unit, the reaction vessel may be disposed of as household waste due to the gelled mass in the interior of the vessel and does not require any costly disposal. Preferably the chemical reaction with the binding agent is designed to take place with a time delay relative to the endothermal reaction between the liquid and the reactant, so that a complete reaction between the liquid and the reactant is ensured. To this end, it is advantageous to encapsulate the binding agent with a liquid-soluble material stored in the interior of the reaction vessel or to deliver it, with a time delay, into the interior of the reaction vessel via an additional mechanism attached to the reaction vessel. In the case of water as the liquid, xanthan is preferably suitable as a binding agent.

In principle, the cooling unit may be fluidically connected to, and used with, a heat exchanger for any applications. Heat exchangers providing cooling surfaces or cooling mats are possible, as are cooling vessels or cooling barrels to identify just a few applications. The cooling unit is suitable to be a cold source of heat exchangers which are integrated in stationary or portable cooling systems.

BRIEF DESCRIPTION OF THE INVENTION

The invention is described by way of example hereinafter without limitation, using an exemplary embodiment with reference to the drawing, in which.

DETAILED DESCRIPTION OF THE INVENTION

Figure 1:
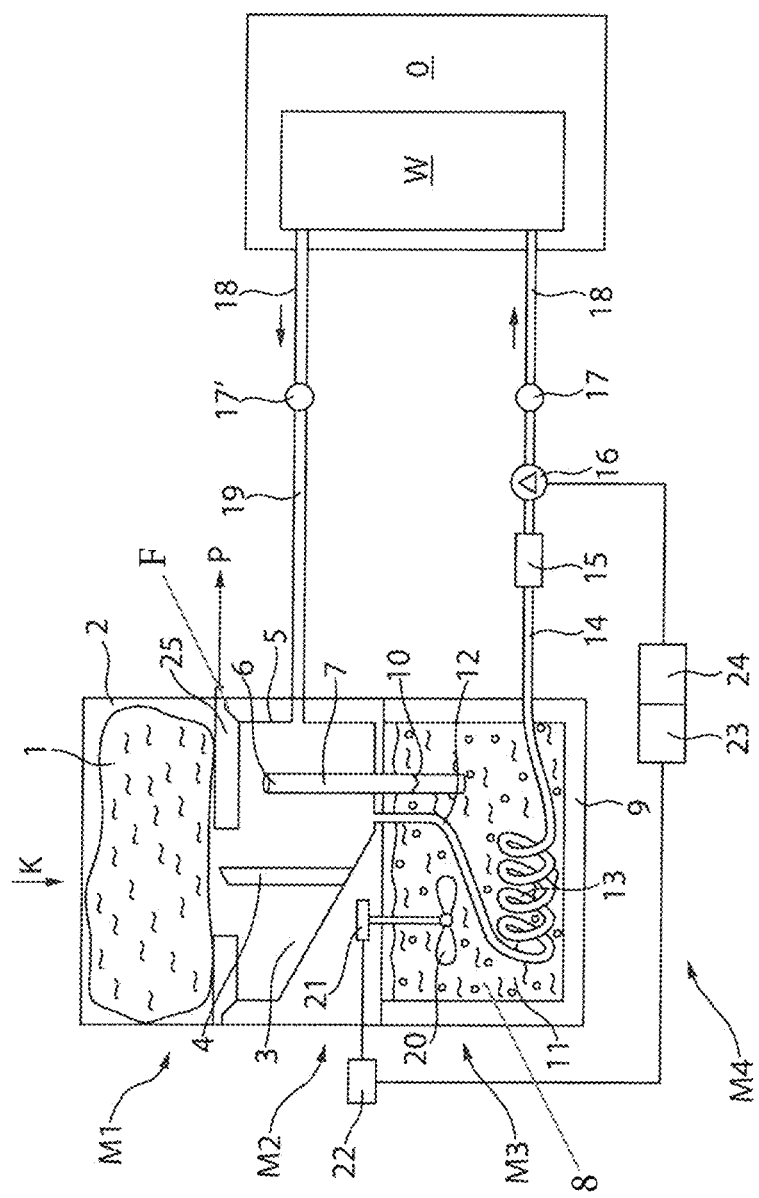
FIG. 1 shows a schematic view of a cooling unit according to the invention for controlling the temperature of a heat exchanger integrated in an oxygenator in the state before activating the cooling function.

FIG. 1 illustrates in schematic view of a cooling unit K according to the invention for providing a cooled heat transfer liquid for operating a heat exchanger W which is preferably part of an oxygenator O.

The cooling unit K has four modules M1 to M4. At least the modules M1-M3 thereof are able to be assembled vertically to be one above the other according to the modular principle. The module M1 has a reservoir 1 for a liquid which preferably is water. Preferably the reservoir 1 has a plastic bag or plastic canister filled with water and which is at least partially surrounded by a first housing 2 for protection and for being mechanically joined to the module M2 located therebelow.

The second module M2, which is arranged vertically below the first module M1, comprises an expansion tank 3 in which a functional means 4 which is an object, for example a needle, pin etc., tapering vertically upwardly to a sharp edge, which is fixed. The expansion tank 3 is surrounded by a second housing 5. An overflow 6, having a fluid connection 7, feeds vertically from above into the reaction vessel 8 of the third module M3, which is surrounded by a third housing 9 protruding vertically from below into the interior of the expansion tank 3. The fluid connection 7 is a pipeline open on both sides which has a non-return valve 10 which prevents an entry of liquid from the reaction vessel 8 into the expansion tank 3. A granular reactant 11, which preferably is granular urea, is stored in the reaction vessel 8.

Moreover, a fluid line 12 discharges into the bottom region of the expansion tank 3 with the fluid line extending further inside the reaction vessel 11, to preferably form coiled lines 13, in order to produce a fluid line surface which is as large as possible inside the reaction vessel 8. The fluid line 12 is fluid light and leads outwardly through the third housing 9 and also functions as an outlet line 14 of the cooling unit K. The fluid line 12 extending in the interior of the reaction vessel 9. In particular the coiled lines 13 which are located therein, are produced from a material which is very effective at conducting heat, preferably from metal, whereas the fluid line along the outlet line 14 is a material which is a poor heat conductor and resilient, for example plastics.

A filter unit 15, which is preferably a bacterial filter, is inserted along the outlet line 14. A fluid pump 16, which preferably is a peristaltic pump, is downstream from the filter unit 15 along the outlet line 14. A releasable fluid-tight coupling 17 is downstream from the filter unit which has a fluid-tight connection to a hose system 18 of the heat exchanger W.

Similarly, the hose system 18 is connected, by a releasable fluid-tight coupling 17', to the inlet fluid line to inlet line 19 into the expansion tank 3 of the cooling unit K.

The third module M3 has an agitator 20 coupled, via a releasable gear unit 21, to a drive motor 22. The drive motor 22, the fluid pump 16, and an electronic control unit 23, in combination with an electrical energy source 24, is a fourth module M4 which operates the drive motor 22 and the fluid pump 15, and is surrounded by a fourth housing, not illustrated further.

The first and second modules M1, M2 are vertically spaced apart by a spacer 25 so that the functional means 4, in the form of an object tapering vertically upwardly, does not contact the reservoir 1 contained inside the first module M1. The spacer 25 slides between the first and second module M1, M2 and preferably is secured by a latching mechanism (not shown) against slipping out to the side in an uncontrolled manner.

For activating the cooling unit K it is imperative that the spacer 25 is able to be removed to the side from the vertical module assembly M1, M2, for example by manually pulling out to the side as illustrated arrow P.

Figure 2:
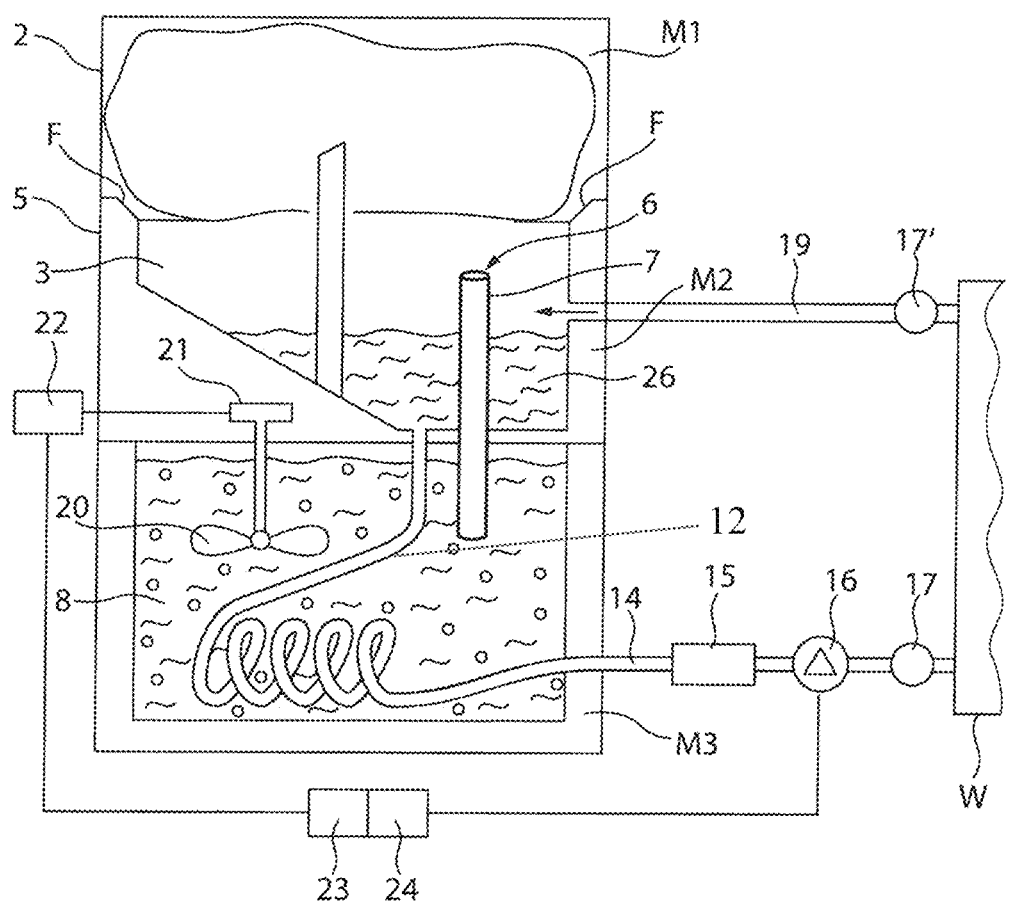
FIG. 2 shows a schematic view of the cooling unit after activating the cooling function.

FIG. 2 illustrates the state after the spacer 25 has been removed to the side from the modular stack assembly. As a result of the missing spacer 25, the reservoir 1 drops down vertically together with the first housing 2, whereby the upwardly tapering functional means 4 locally perforates the reservoir 1. In order to ensure that the dropping and joining process of the first module M1 onto and into the second module M2 takes place in a specific manner, the first and second housings 2, 5 on their respective vertically facing sides have peripheral joining contours F at the side.

As a result of the mechanically initiated perforation of the reservoir 1, the entire liquid contents of the reservoir 1 flows into the expansion tank 3. Approximately 80% of the quantity of liquid stored in the reservoir 1 flows via the overflow 6 and the fluid connection 7 into the reaction vessel 8 and initiates an endothermal chemical reaction with the reactant 11, so that cooling takes place inside the reaction vessel 8. A remaining proportion 26 of the liquid remains inside the expansion tank 3 and serves as heat transfer liquid for operating the heat exchanger W. At the same time as the removal of the spacer 25 and, as a result, the gravity-driven perforation of the reservoir 1, both the fluid pump 16 and also the drive motor 22, which drives the agitator 20 via the gear unit 21, are activated by the electronic control unit 23.

The fluid pump 16 operates as a suction pump that suctions the liquid located inside the expansion tank 3, and a remaining proportion 26, through the fluid line 12 which is cooled due to the cooling inside the reaction region 8. In order to optimize the heat transfer from the liquid conveyed inside the fluid line 12 to the liquid/reactant mixture cooling in the path of the endothermal reaction, it is imperative to ensure a heat transfer contact surface is as large as possible between the fluid line 12 and the liquid-reactant mixture present in the interior of the reaction vessel 8. To this end, the line path of the fluid line 12 in the interior of the reaction vessel 8 is configured at least in some sections to be helical or in a helical manner.

The cooled liquid is pumped via the outlet line 14 through the filter unit 15 into the heat exchanger W. After exiting the heat exchanger W, the outflowing heat transfer liquid passes via the inlet line 19 back into the expansion tank 3 from which liquid is suctioned for the purpose of the cooling thereof via the fluid line 12 back into the region of the reaction vessel 8.

Advantageously the first, second and third modules M1, M2, M3 are disposable articles, and the fourth module M4 comprising the electrical components may be reused as often as desired. The filter unit 15 is preferably an integral component of the third module M3 and thus also part of a disposable article. For reasons of weight and cost, the modules M1, M2 and M3 are produced from a plastics lightweight packaging material, which may also be sent for material recycling. Additionally the expansion tank 3 and the reaction vessel 8, formed by the modules 2 and 3, are provided with a liquid-tight coating on the inner wall.

Figure 3:
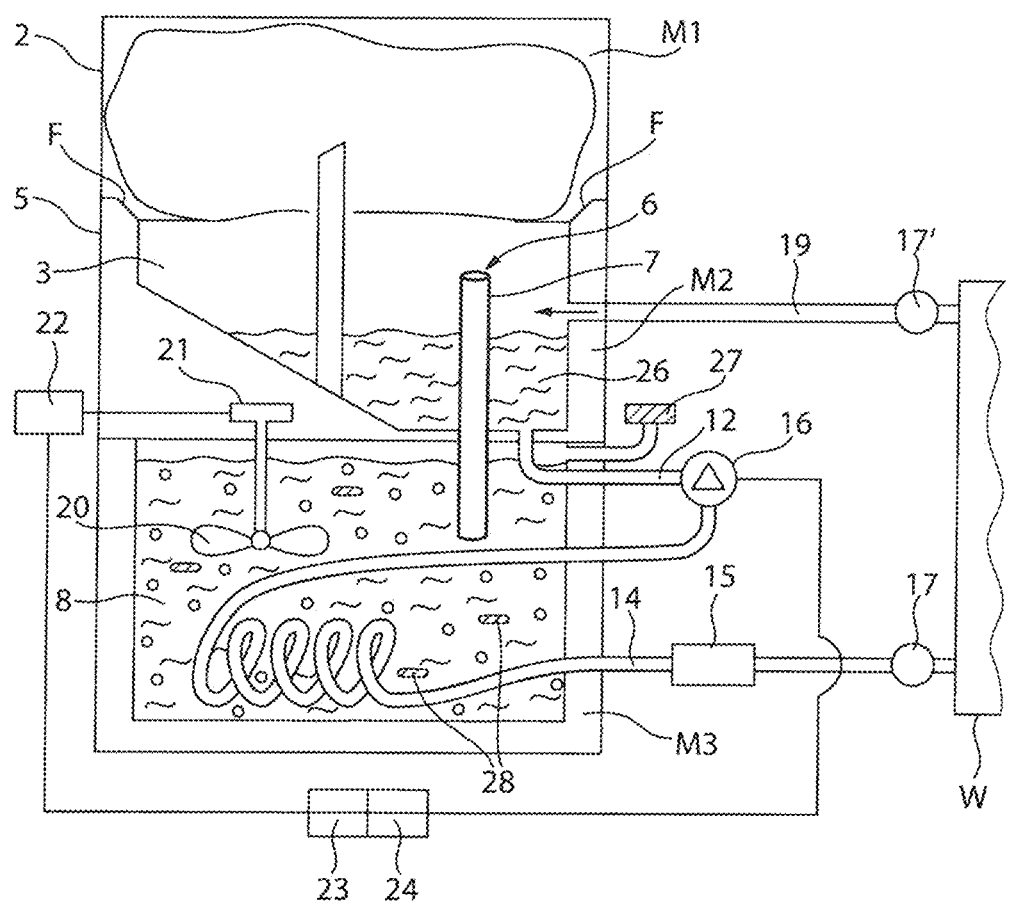
FIG. 3 shows an alternative embodiment of the cooling unit according to the invention.

A further preferred embodiment of the configuration of the cooling unit in the state of the directly vertically positioned modules M1, M2 and M3 is illustrated in FIG. 3, comparable with the view in FIG. 2. All of those components, which are identical to the already described components, are provided with the already introduced reference numerals.

In contrast to the view in FIG. 2, the fluid line 12 leads directly downstream to its fluid connection with the expansion tank 3 to outside the reaction vessel 8, where the fluid pump 16 is incorporated along the fluid line 12 and suctions liquid from the expansion tank 3 into the fluid line 12. Downstream of the fluid pump 16, which is outside the reaction vessel 8, the fluid line 12 leads back again into the reaction vessel 8 The fluid line 12 is helically shaped to provide a heat transfer contact surface which is as large as possible ensuring an effective cooling of the liquid conveyed inside the fluid line 12.

The filter unit 15 is arranged along the outlet line 14 from the reaction vessel 8. The filter unit is a bacterial filter, for example a *Legionella* filter, ensuring that the cooled liquid is germ-free, so that the heat exchanger W inside the oxygenator is not contaminated.

Additionally, the reaction vessel 8 has a vent 27 in the upper region, with a hydrophobic filter ensuring a complete and rapid filling of the reaction vessel 8 which prevents an uncontrolled escape of liquid to the outside.

After the cooling process is complete, a binding agent 28, preferably xanthan, which is stored in the reaction vessel 8, causes gelling of the liquid-reactant mixture so that a simple disposal of the modules 1, 2 and 3 is possible, such as for example household waste. To this end, the binding agent 28 is encapsulated with a liquid-soluble material which completely dissolves after a certain residence time inside the liquid and releases the binding agent inside the reaction vessel.

LIST OF REFERENCE NUMERALS

1 Reservoir
2 First housing
3 Expansion tank
4 Functional means
5 Second housing
6 Overflow
7 Fluid connection
8 Reaction vessel
9 Third housing
10 Non-return valve
11 Reactant
12 Fluid line
13 Coiled line
14 Outlet line
15 Filter unit
16 Fluid pump
17, 17' Releasable fluid-tight coupling
18 Hose system
19 Inlet line
20 Agitator
21 Gear unit
22 Drive motor
23 Electrical control unit
24 Electrical energy source, battery
25 Spacer
26 Remaining proportion of liquid
27 Venting unit
28 Binding agent
W Heat exchanger
O Oxygenator
M1, M2, M3, M4 Modules
P Direction of arrow
K Cooling unit
F Joining contour

The invention claimed is:

1. A cooling unit for a heat exchanger, integrated into an oxygenator comprising:
   a reservoir in which a liquid is stored;
   a reaction vessel comprising a reactant which in conjunction with the liquid, can initiate an endothermal reaction;
   means for providing a fluidic access between the reservoir and the reaction vessel; and
   a fluid line extending at least in part inside the reaction vessel and which has an inlet line and an outlet line, which are each connectable to a hose system of the heat exchanger, and which, together with a hose system of the heat exchanger, are at least part of a fluid circuit;
   an expansion tank having an overflow into which the liquid from the reservoir flows after fluidic access is generated between the reservoir and the reaction vessel, so that overflow provides a fluid connection to the reaction vessel through which a proportion of stored liquid in the reservoir passes into the reaction vessel to initiate an endothermal reaction with the reactant, so that and the fluid line is fluidically connected to the expansion tank, into which a remaining proportion of the stored liquid from the reservoir passes; and
   a fluid pump located along the fluid line, so that liquid from the expansion tank passes into the fluid line which extends at least in part inside the reaction vessel.

2. The cooling unit according to claim 1, comprising:
a non-return valve located along the fluid connection of the overflow which prevents a return flow of liquid from the reaction vessel into the expansion tank.

3. The cooling unit according to claim 1, wherein:
the fluid pump is a suction unit located along the fluid line outside the expansion tank and reaction vessel.

4. The cooling unit according to claim 1, wherein:
the fluid pump comprises a peristaltic pump.

5. The cooling unit according to claim 1, wherein:
the fluid line downstream of a region extends inside the reaction vessel which provides the outlet line along which a filter is positioned which extends outside the reaction vessel.

6. The cooling unit according to claim 5, wherein:
the filter unit is a *Legionella* filter.

7. The cooling unit according to claim 1, wherein:
the inlet line of the fluid line feeds into the expansion tank, and the fluid circuit includes the expansion tank, the fluid line and the hose system of the heat exchanger, through which a remaining proportion of the liquid circulates as heat transfer liquid of the heat exchanger.

8. The cooling unit according to claim 1, comprising:
the reservoir is disposed vertically above the expansion tank; and
means for providing fluidic access which is a sharp-edged object positioned vertically below the reservoir; and
a spacer located between the reservoir and the expansion tank which vertically spaces apart the reservoir above the means for providing fluidic access; and
upon removal of the spacer, the reservoir is driven by gravitational force to contact the means for providing fluidic access which mechanically penetrates the reservoir, so that the liquid stored in the reservoir pours into the expansion tank.

9. The cooling unit according to claim 1, wherein:
the means for providing fluidic access is fixedly positioned on the expansion tank.

10. The cooling unit according to claim 1, comprising:
an agitator inside the reaction vessel which is driven by a mechanical interface by a drive motor outside the reaction vessel.

11. The cooling unit according to claim 1, wherein:
at least the reservoir, the means for providing fluidic access and the reaction vessel are disposable articles.

12. The cooling unit according to claim 11, wherein:
the filter unit and the agitator are parts of the disposable article and the drive motor and the fluid pump are connected to an electrical energy source and an electrical controller which is a modular for a mechanical attachment to the disposable article.

13. The cooling unit according to claim 1, wherein:
the heat exchanger is integrated into a cooling system.

14. The cooling unit according to claim 1, wherein:
a binding agent is stored inside the reaction vessel, which upon coming into contact with the liquid entering into the reaction vessel a gel is formed with the liquid.

15. The cooling unit according to claim 1, wherein:
at least the reservoir and the reaction vessel comprise a plastic packaging material.

16. The cooling unit according to claim 15, wherein:
at least an inner wall of the reaction vessel which contacts the liquid is coated with a liquid-tight coating.

17. The cooling unit according to claim 1, wherein:
the reaction vessel includes a vent.

* * * * *